United States Patent [19]

Miyata et al.

[11] Patent Number: 4,565,580
[45] Date of Patent: Jan. 21, 1986

[54] SUBSTRATE CONSISTING OF REGENERATED COLLAGEN FIBRILS AND METHOD OF MANUFACTURING SAME

[75] Inventors: Teruo Miyata, Tokyo; Shinichi Namiki, Ome, both of Japan

[73] Assignee: Koken Co., Ltd., Tokyo, Japan

[21] Appl. No.: 586,944

[22] Filed: Mar. 7, 1984

[30] Foreign Application Priority Data

Mar. 10, 1983 [JP] Japan ................................. 58-39597

[51] Int. Cl.⁴ ............................................ C08L 89/00
[52] U.S. Cl. ................................. 106/124; 260/123.7
[58] Field of Search ...................... 260/123.7; 106/124

[56] References Cited

U.S. PATENT DOCUMENTS

| | | | |
|---|---|---|---|
| 2,919,998 | 1/1960 | Klevens et al. | 106/124 |
| 2,919,999 | 1/1960 | Reissmann et al. | 106/124 |
| 2,920,000 | 1/1960 | Hochstadt et al. | 106/124 |
| 2,935,413 | 5/1960 | Veis et al. | 106/124 |
| 3,071,483 | 1/1963 | Tu et al. | 106/124 |
| 3,551,535 | 12/1970 | Henderson et al. | 106/124 |
| 3,632,361 | 1/1972 | Battista | 106/124 |
| 3,806,350 | 4/1974 | Kuhn et al. | 106/124 |
| 4,279,812 | 7/1981 | Cioca | 106/124 |
| 4,420,339 | 12/1983 | Kato | 106/124 |

OTHER PUBLICATIONS

Methods of Enzymology, vol. 82, pp. 499–544 (1982), Academic Press.
Develop., Growth and Differ., 23 (2), pp. 157–184 (1981), "In Vitro Orientation of Fibroblasts and Myoblasts on Aligned Collagen Film".

Primary Examiner—James J. Bell
Attorney, Agent, or Firm—Armstrong, Nikaido, Marmelstein & Kubovcik

[57] ABSTRACT

A substrate consisting essentially of regenerated collagen fibrils is provided which is in the form of a bead, or microsphere and comprises irregularly entangled regenerated collagen fibrils each having a diameter of 10–1000 m$\mu$ and an aqueous solution existing between the regenerated collagen fibrils, the content of the regenerated collagen fibrils being 20–0.01 wt. %. The substrate can be used for cell culture or for measuring adhesion activity of blood platelet.

According to one method of manufacturing the collagen beads, an acidic aqueous collagen solution is dispersed in a water-immiscible organic solvent in the form of numerous droplets to form an emulsion, and the droplets are then coagulated by addition of a water-miscible organic solvent and an alkali to the emulsion.

According to another method of manufacturing the collagen beads or microspheres, a neutral collagen solution is dispersed in a water-immiscible organic solvent in the form of numerous droplets to form an emulsion, and the droplets are then coagulated by raising the temperature of the emulsion to 30° C.–40° C. The collagen beads or microspheres prepared by the methods described above may be cross-linked by hexamethylenediisocyanate or glutaraldehyde.

9 Claims, 2 Drawing Figures

SUBSTRATE CONSISTING OF REGENERATED COLLAGEN FIBRILS AND METHOD OF MANUFACTURING SAME

BACKGROUND OF THE INVENTION

1. Field of the Invention

The present invention relates to a substrate consisting essentially of regenerated collagen fibrils, and more particularly it relates to the substrate of regenerated collagen fibrils useful for cell culture and as a carrier for measuring adhesion activity of blood platelets.

2. Brief Description of the Prior Art

The technology for utilizing useful substances obtained by culturing animal cells in a large amount and isolating the products has been watched with keen interest as one of the fields of biotechnology. Also, in the academic studies of artificial organs, studies have been actively performed for artificial organs of the type that the animal cells are incorporated therewith.

In both cases, it is most important to carry out a mass proliferation by culturing the cells removed from living bodies while keeping the physiological activities of the cells. Collagen plays a vital role as a supporting substance, namely substrate, for cells which constitute organs and tissues in the living body. Accordingly, it can be said that collagen is the best and an excellent substrate for cell culture among the existing substances.

In general, animal cells grow and proliferate while adhering to the substrate, and thus the existence of the effective substrate is essential for maintaining the activities of the cells. For the mass culture and mass proliferation of animal cells, the shape of the substrate in the form of a fine particle rather than a flat plate is remarkably advantageous since it is necessary for the substrate to have a very large surface area. Thus, recently, beaded fine particles or microsphere carriers are being employed; for example, a crosslinked dextran has been developed and marketed as beaded substrate for the mass culture of cells, (see Catalogue Cytodex 1, "Beaded Microcarrier for Cell Culture" from Pharmacia Japan Co., Ltd.).

As described above, collagen plays a role as substrate a for various types of cells in the living body and has been utilized as a substrate for cell culture. However, the conventional collagen has only been used as a substrate coated on the surface of various articles of plastics or glass, or also, has only been used for cell culture on the surface or inside of a gel in the form of collagen gel obtained by neutralizing an acid solution of collagen under physiological conditions.

OBJECTS AND SUMMARY OF THE INVENTION

The object of this invention is to provide a substrate consisting essentially of regenerated collagen fibrils, which is very useful for a mass culture and a mass proliferation of animal cells.

Another object of this invention is to provide a substrate containing regenerated collagen fibrils which can be utilized for measuring adhesion activity of blood platelets. A further object of this invention is to provide a method of manufacturing a substrate consisting essentially of regenerated collagen fibrils. The present inventors have noticed that the mass culture of cells is made easy by remarkably increasing the substrate surface to which the cell adheres by the formation of beaded, or spherical, collagen substrates, as compared with the conventional substrate surface, and as a result of strenuous efforts, this invention has been made.

Thus, according to this invention there is provided a substrate (hereinafter referred to as collagen beads) consisting essentially of irregularly entangled regenerated collagen fibrils each having a diameter of 10–1000 m$\mu$ with an aqueous solution existing between the regenerated collagen fibrils, the content of the regenerated collagen fibrils being 20–0.01 wt. %.

According to this invention, the above-mentioned collagen beads can be obtained in two ways; (1) an acidic aqueous solution of collagen is dispersed in a water-immiscible organic solvent in the form of numerous droplets to form an emulsion, and the droplets are then solidified, or coagulated, by addition of a water-miscible organic solvent and an alkali to the emulsion and (2) neutral aqueous collagen solution is dispersed in a water-immiscible organic solvent in the form of numerous droplets to form an emulsion at a temperature of 0° C.–25° C., and the droplets are then solidified by raising a temperature to 30° C.–40° C.

DETAILED DESCRIPTION OF THE PREFERRED EMBODIMENTS

Figure 1:
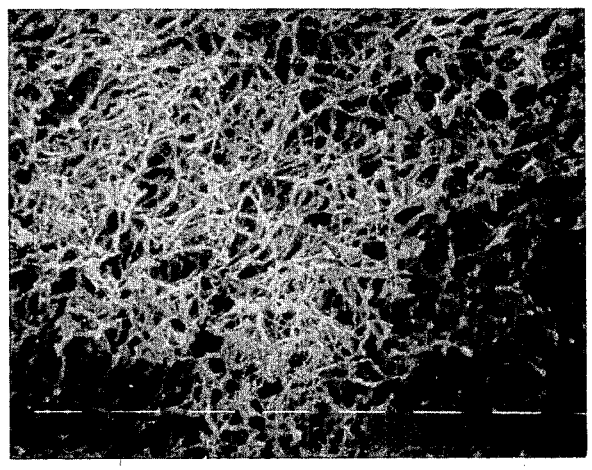
FIG. 1 is a scanning electron-microscopic photograph (magnification: 8000) showing the shape of the regenerated collagen fibrils contained in the collagen beads which were obtained by a method of Example 1.

The collagen beads according to this invention contain 20–0.01 wt. % of the regenerated collagen fibrils each having a diameter of 10–1000 m$\mu$. The regenerated collagen fibrils are irregularly entangled as can be observed by a scanning microscopic picture. Between the regenerated collagen fibrils, there exists an aqueous solution which can be replaced by any other water-miscible liquids. For instance, in the case that a physiological salt solution exists between the regenerated collagen fibrils, when the collagen beads are soaked in an aqueous medium for a cell culture, the physiological salt solution is replaced by this aqueous medium. Collagen used according to this invention may be an acid-soluble collagen or neutral salt-soluble collagen obtained by extracting the collagen tissue of young animals with an aqueous neutral salt solution or aqueous dilute acid solution.

On the other hand, insoluble collagens exhibiting no solubility in these extraction procedures can be solubilized by a treatment with proteolytic enzymes such as pepsin to form an enzyme-solubilized collagen (atelocollagen) or by an alkali-treatment. These solubilized collagens may also be used according to this invention. Here, the atelocollagen is a name given rather recently to a collagen from which telopeptides have been removed by treatment with proteolytic enzymes. The above mentioned insoluble collagens are made insoluble owing to the intermolecular crosslinkages formed through telopeptide which exists at the terminal of the molecule. When pepsin, a proteolytic enzyme, acts on the insoluble collagen, telopeptide alone is digested, and the intermolecular crosslinkages are broken and thus the insoluble collagen is solubilized to yield atelocollagen. Atelocollagen can also be obtained from soluble collagen extracted by an aqueous solution of dilute acid or neutral salt and by the treatment with pepsin.

Water-immiscible organic solvents used according to this invention may include toluene, carbon tetrachloride, chloroform, cyclohexane, ether, petroleum ether and benzene and the like. It is desirable to make, by properly mixing these organic solvents, the specific gravity of a solvent as close as possible to the specific gravity of an aqueous collagen solution to be dispersed to prevent the floating or deposition of the aqueous solution of collagen when dispersing the collagen solution into droplets.

For the formation of an emulsion by dispersing the acidic aqueous solution of collagen in the form of droplets, conventional methods can be used to prepare the emulsion by stirring or vibrating the aqueous solution of collagen in a water-immiscible organic solvent. The size of dispersed droplets can be adjusted by controlling the degree of stirring or vibration. It is desirable that the amount of the collagen solution used be equal to or less than that of the organic solvent. It is desirable that the concentration of the aqueous collagen solution be less than 5%, since a solution having a concentration above 5% is too viscous, and it is difficult to make a dispersion.

In order to improve the stability of the resulting emulsion, it is desirable to add a small amount of a surface active agent. Preferred surfactants which may be used are of the nonionic type, and as examples may be mentioned SPAN-series (a registered trademark of Atlas Powder Co., Ltd. in the U.S. for sorbitan fatty acid esters) or TWEEN-series (a registered trade mark of Atlas Powder Co., Ltd. in the U.S. for polyoxyethylene sorbitan fatty acid esters). The amount of the surfactant used is preferably less than 0.1% on the basis of the total weight of the mixture of the organic solvent and the collagen solution.

According to the method of this invention, the alkali agents to be used for solidifying the droplets may be basic substances such as ammonia, disodium hydrogenphosphate ($Na_2HPO_4$), sodium hydroxide and the like. Moreover, the water-miscible organic solvent to be used for solidifyinng the droplets may be methanol, ethanol, acetone and the like. These alkali agents and organic solvents can be used such that they are added simultaneously to the emulsion or the organic solvent is added before the alkali is added. The amount of the water-miscible organic solvent used is preferably above 50% on the basis of the weight of the emulsion. The amount of alkali used may be that amount required for neutralizing the droplets of dispersed collagen solution.

A particularly preferred method of solidifying the droplets is to add a mixture of an aqueous solution of a basic substance and a water-miscible organic solvent, to the emulsion. A preferred mixture is a the mixture of aqueous ammonia and any one of methanol, ethanol and acetone, and the ammonia content is usually 1–2%. After the addition of the alkali and the water-miscible organic solvent, the emulsion is slowly stirred for more than one hour, thereby solidifying the droplets of the aqueous solution of collagen, and in this case, it is advantageous that a silicone oil has been previously applied on the wall of the vessel used, thereby preventing the solidified collagen beads from adhering to the wall of the vessel.

For the formation of an emulsion by dispersing a neutral aqueous collagen solution into droplets, principally the dispersion procedure similar to that for the acidic collagen solution can be applied. Neutral aqueous collagen solution can be prepared by dissolving acid soluble collagen or atelocollagen in a buffer solution of pH 6.0–8.0 having an osmolarity of 200–400 mOsm/l at a temperature of 0° C.–15° C. Phosphate buffer solution is preferably used for making a neutral aqueous collagen solution. A neutral aqueous collagen solution is added into a water-immiscible organic solvent containing surfactant at a temperature of 0° C.–25° C. and stirred or vibrated to form droplets. Even in a neutral aqueous collagen solution, a collagen concentration of less than 5% is desirable, because the viscosity of a solution having a concentration above 5% is extraordinarily high. The amount of surfactant used in the dispersion process is exactly the same as that used in the acidic aqueous collagen solution procedure.

In order to solidify the droplets of neutral aqueous collagen solution, the temperature of the mixture is raised to 30° C.–40° C. The collagen solution of the droplets coagulates at a temperature of 30° C.–40° C. to form collagen fibril.

The solidified collagen beads prepared from the acidic or neutral aqueous collagen solution may be crosslinked by hexamethylenediisocyanete (HMDIC) or glutaraldehyde. The crosslinking makes the beads stable against heat denaturation. In addition, while the beads without crosslinking sometimes aggregate during storage, crosslinked beads remain stable during storage in a bottle. The solidified collagen beads prepared from acidic or neutral aqueous collagen solutions can be separated by using a centrifuge or by using a screen, and are washed with water-miscible organic solvents, such as methanol, ethanol, acetone and the like, followed by repeated water washing. The collagen beads thus obtained are somewhat non-uniform in particle size and it is possible to make the particle size uniform by screening to obtain e.g. fractions over 48 mesh, between 48–100 mesh, between 100–200 mesh, and under 200 mesh. The collagen beads according to the invention contain the irregularly entangled regenerated collagen fibrils as mentioned above. Thus, by the use of the collagen beads suspended in a culture solution as substrates for cell culture, it is possible to have an enlarged area of substrate surface effective for cells adhesion, and the mass culture of cell can easily be carried out. In the case of using an aqueous solution of collagen having a concentration, for example, of 1%, the finally obtained collagen beads after water washing have a collagen content of about 1%, and the remainder, 99%, comprises mainly water.

Accordingly, when the beads are equilibrated in a culture solution, a great portion of water in the beads can be replaced by the culture medium, and the specific gravity of the beads becomes nearly equal to that of the culture solution, and the beads move slowly by slow stirring during the culture, with the result that the cells adhering to the beads are prevented from being damaged.

The collagen beads according to this invention can also be utilized for measuring the adhesion activity of blood platelets. It is known that blood platelets adhere to the collagen fibrils, and also cause a coagulating reaction. Accordingly, when a column is filled with the collagen beads according to this invention, and a sample solution containing blood platelets (for example, blood admixed with anti-coagulants such as sodium citrate, EDTA; or platelet rich plasma) is passed through the column, it is possible to measure the adhesion of platelets by counting the number of the blood platelets adhering to the collagen beads in the column. Based on this adhesion activity, it is possible to determine the coagulative activity of the test blood, and the method can be used for one method of diagnosis of diseases relating to blood, such as thrombosis. In the manufacture of collagen beads according to this invention, it is possible to obtain germfree beads under germfree conditions, while the collagen beads not manufactured under germfree conditions can be sterilized by placing them into a sealed vessel and irradiating with γ-ray, of, preferably, 0.5–1.5 Mrad.

This invention will now be described in detail by way of examples. However, it is to be understood that this invention is not limited to these particular examples.

EXAMPLE 1

The fresh dermis removed from a calf skin was finely divided with a micro-cutter manufactured by Stephan Co., Ltd. The finely divided powders were repeatedly washed with a 0.1 M aqueous solution of sodium acetate, followed by washing with water. The finely divided powders were then extracted with a 0.5 M aqueous solution of acetic acid, and the residual insoluble collagen was then collected by filtration through a glass filter. The filtrate containing the acid soluble collagen was subjected to dialysis against 0.02 M solution of disodium hydrogen phosphate ($Na_2HPO_4$) and thus the acid soluble collagen was precipitated as collagen fibrils. After repeatedly washing, the collagen fibrils were dissolved in 0.01 N-HCl so that the collagen concentration was adjusted to 1 wt. %. The resulting acid-soluble collagen solution had a specific gravity of abut 1.00.

On the other hand, a mixed solvent was prepared by mixing toluene 800 ml and chloroform 220 ml in a vessel. The specific gravity of the mixed solvent was nearly equal to that of the above acid-soluble collagen solution. To the mixed solvent were added 0.1%, based on the weight of the mixed solvent, of Span 20 (registered trademark of Atlas Powder Co., Ltd. for a nonionic surface active agent of sorbitan monolauric acid ester type) and further 300 ml of the above-mentioned 1% acid soluble collagen aqueous solution. Thereafter, the content of the vessel was stirred vigorously for about 30 seconds, and then immediately one liter of ethanol containing 2% of ammonia was added. The content in the vessel was stirred slowly for 2 hours, and solidified collagen beads were obtained in a dispersed state. The liquid dispersion of the beads was filtered by a 200-mesh screen of stainless steel.

The beads obtained were soaked in 500 ml of ethanol and were filtered. These beads were further washed 3 times each with one liter of distilled water. Then, the beads were fractionated for measuring the particle size distribution with screens of stainless steel having openings of 48, 100 and 200 mesh. The results are given below, in terms of wt. %.

about 30% . . . oversize above 48 mesh
about 50% . . . fraction between 48–100 mesh
about 10% . . . fraction between 100–200 mesh
about 10% . . . undersize below 200 mesh FIG. 1 shows a scanning electron-microscopic photograph of the structure of the collagen fibrils contained in the collagen beads. As can be seen from FIG. 1, the regenerated collagen fibrils were irregularly entangled.

These fractionated beads with different particle sizes were placed into sealed bottles, and irradiated with γ-rays of 0.75 Mrad for sterilization. The collagen beads of the fraction between 48–100 mesh were used for a culture test of fibroblast of human dermis. The cells adhered to the beads after a few hours, and they proliferated so as to cover the entire surface of the beads after 5 days. These beads were found to be an excellent substrate for the cells.

Figure 2:
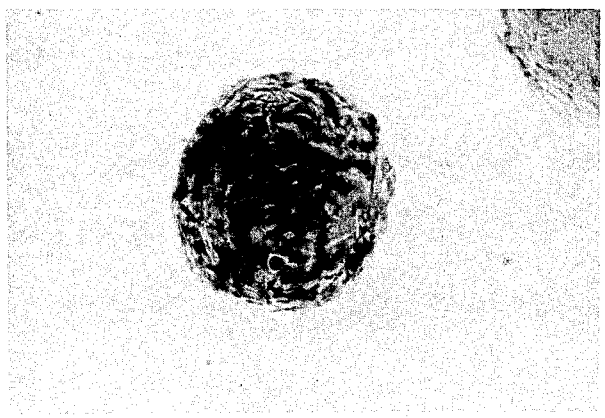
FIG. 2 is a phase microscopic photograph (magnification: 70), showing the particle structure of the collagen beads of Example 1 after being used in the culture test in Example 1.

FIG. 2 shows the phase microscopic photograph showing a particle structure of the collagen beads after the use in the culture test.

EXAMPLE 2

100 g of the insoluble collagen obtained as the residue after extracting the acid soluble substance from the dermis of the calf skin in Example 1 were collected in a wet state, and one liter of 0.5 M acetic acid and 0.1 g of pepsin were added thereto. The resulting mixture was stirred at 20° C. for 3 days. By this treatment, the insoluble collagen was dissolved to yield viscous, pepsin-solubilized collagen (atelocollagen).

After filtering the atelocollagen through a glass filter, the pH of the filtrate was adjusted to 7.5 by adding an aqueous sodium hydroxide solution, thereby forming a fibrous precipitate. After separating by a centrifuge, the precipitate was washed with distilled water three times, and was then dissolved in a sufficient amount of 0.01 N-HCl to prepare a solution containing 2% of collagen (specific gravity: about 1.01).

A mixed solvent (specific gravity: about 1.080) was prepared by mixing toluene (400 ml) and chloroform (115 ml) and to the solvent mixture was added a non-ionic surface active agent, Tween 80 (Tween is a registered trade mark of Atlas Powder Co., Ltd. for nonionic surfactants of'ethylene oxide condensate type of sorbitan mono-oleate) in an amount of 0.1 wt. % based on the weight of the solvent, and also 150 ml of the above-mentioned 2% collagen solution. The resulting solution was homogenized by a homogenizer with high-speed stirring of 10,000 r.p.m. for one minute, and was immediately mixed with methanol containing 2 wt. % of ammonia and stirred slowly. As a result, solidified fine beads were obtained. These beads were fractionated using stainless wire screens, followed by washing with methanol three times and further with water three times. Similarly to Example 1, the particle size distribution was measured, and the results are given below, in terms of wt. %.

about 10% . . . oversize above 48 mesh
about 60% . . . fraction between 48–100 mesh
about 20% . . . fraction between 100–200 mesh
about 10% . . . undersize below 200 mesh It has been found that these beads are composed of collagen fibrils when observed by a scanning electron microscope. Each of the fractions of the beads was placed in a sealed glass bottle and irradiated with γ-rays of 1 Mrad for sterilization. Among the fractions, the fraction of the beads between 48–100 mesh screens and fibroblasts of human dermis were used for suspension culture and these collagen beads proved to be an excellent substrate.

EXAMPLE 3

Pepsin-solubilized collagen (atelocollagen) obtained in the same procedure as in Example 2 was dissolved in 0.01 N-HCl to prepare a solution containing 1% of the collagen. The 1% atelocollagen solution was passed through an autoclave-sterilized filter having a fine pore diamether of 0.45 μm to prepare a germfree solution.

On the other hand, to a mixed solvent of toluene (400 ml) with chloroform (110 ml) was added 0.1% of a nonionic surfactant, Span 20 (see, Example 1), and the mixed solvent was passed through a disinfected 0.22 μm microfilter for sterilization. To the resulting sterilized mixed solution was added 100 ml of disinfected 1% atelocollagen solution, and the solution was stirred violently.

Immediately thereafter, to the solution was added 500 ml of ethanol sterilized by being passed through a microporous filter having a diameter of 0.22 μm. After the solution was stirred slowly for 2 hours, 10 ml of an aqueous 2%-ammonia solution were added to the solution, followed by stirring slowly for a further 2 hours. As a result, fine beads solidified in a dispersed state were obtained. The beads obtained were treated similarly to Example 1 and were washed with ethanol, followed by washing with water, further being fractionated. The results are given below, in terms of wt. %.

about 25% . . . oversize above 48 mesh
about 55% . . . fraction between 48–100 mesh
about 10% . . . fraction between 100–200 mesh
about 10% . . . undersize below 200 mesh The collagen beads thus obtained have been found to be made up of regenerated collagen fibrils in the observation by a scanning electron microscope, and have been found to be an excellent substrate in a cell culture test.

EXAMPLE 4

Atelocollagen obtained in the same way as in Example 2 was dissolved in 0.1 M phosphate buffer solution, pH 7.3, to make the collagen concentration 1% at 10° C. The resulting neutral aqueous atelocollagen solution was added to a mixed solvent of toluene (400 ml) and chloroform (110 ml) containing 0.1% of Span 20 and stirred vigorously at 10° C. Immediately thereafter the mixture was warmed to 37° C. and kept at 37° C. for 2 hours to solidify the droplets. The solidified beads were washed with methanol to wash out toluene and chloroform and equilibrated with 0.9% NaCl solution and fractionated similarly to Example I and the results are given below, in terms of wt. %.

about 25% . . . oversize above 48 mesh
about 60% . . . fraction between 48–100 mesh
about 12% . . . fraction between 100–200 mesh
about 3% . . . undersize below 200 mesh The fractionated beads were irradiated with gamma-rays at a total dose of 1.0 Mrad. The beads have been found to be made up of regenerated collagen fibrils and to be an excellent substrate for cell culture.

EXAMPLE 5

Atelocollagen beads were prepared using exactly the same procedure as that of Example 4, but providing crosslinking with hexamethylenediisocyanate (HMDIC). After solidification of the droplets by raising the temperature to 37° C. for 2 hours, the solidified beads were collected by screening through a 200 mesh screen and washed with methanol to remove toluene and chloroform, and thereafter soaked in 0.1% HMDIC in methanol solution for crosslinking at room temperature for 1 hour. After washing with methanol, the beads were equilibrated with 0.9% NaCl aqueous solution and fractionated by screens. The results are given below, in terms of wt. %.

about 20% . . . oversize above 48 mesh
about 50% . . . fraction between 48–100 mesh
about 20% . . . fraction between 100–200 mesh
about 10% . . . undersize below 200 mesh The crosslinked, fractionated beads were gamma-irradiated at 1.0 Mrad for sterilization. The beads thus prepared consisted of regenerated collagen fibril, and were found to be an excellent substrate in cell culture test.

What is claimed is:

1. A collagen-containing substrate in the shape of a microsphere, said microsphere comprising irregularly entangled regenerated collagen fibrils having a diameter of 10–1000 mμ and an aqueous solution existing between the regenerated collagen fibrils, the content of the regenerated collagen fibrils being 20–0.01 wt. %.

2. A method of manufacturing a collagen-containing substrate in the form of microspheres comprising regenerated collagen fibrils and an aqueous solution existing between the regenerated collagen fibrils, said method comprising dispersing an acidic aqueous collagen solution in the form of droplets in a water-immiscible organic solvent to form an emulsion, and then coagulating the droplets by addition of a water-miscible organic solvent and an alkali to the emulsion.

3. A method according to claim 2, wherein the addition of the water-miscible organic solvent and the alkali is carried out simultaneously.

4. A method according to claim 2, wherein the addition of the water-miscible organic solvent is carried out before the addition of the alkali.

5. A method according to claim 2, wherein the coagulated droplets are further subjected to a treatment with a crosslinking agent selected from the group consisting of hexamethylenediisocyanate and glutaraldehyde.

6. A method according to claim 2, wherein the content of the regenerated collagen fibrils in said microspheres is 20–0.1 wt. %.

7. A method of manufacturing a collagen-containing substrate in the form of microspheres comprising regenerated collagen fibrils and an aqueous solution existing between the regenerated collagen fibrils, said method comprising dispersing a neutral aqueous collagen solution in the form of droplets in a water-immiscible organic solvent at a temperature of 0° C.–25° C. to form an emulsion, and then coagulating the droplets by raining the temperature of the emulstion to 30° C.–40° C.

8. A method according to claim 7, wherein the coagulated droplets are further subjected to a treatment with a crosslinking agent selected from the group consisting of hexamethylenediisocyanate and glutaraldehyde.

9. A method according to claim 6, wherein the content of the regeneratd collagen fibrils in said microspheres is 20–0.01 wt. %.

* * * * *